(12) United States Patent
Matsumoto

(10) Patent No.: US 7,871,631 B2
(45) Date of Patent: *Jan. 18, 2011

(54) METHODS OF INHIBITING THE LOWERING OF ANTIHUMAN TNF-α ANTIBODY

(75) Inventor: Takayuki Matsumoto, Fukuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/562,728

(22) Filed: Sep. 18, 2009

(65) Prior Publication Data

US 2010/0008916 A1    Jan. 14, 2010

Related U.S. Application Data

(60) Division of application No. 11/514,225, filed on Sep. 1, 2006, now Pat. No. 7,638,335, which is a continuation of application No. PCT/JP2005/033780, filed on Mar. 1, 2005.

(30) Foreign Application Priority Data

Mar. 1, 2004    (JP)    ............................ 2004-056343

(51) Int. Cl.
*A61K 45/00* (2006.01)
*A61K 47/00* (2006.01)
*A61K 47/44* (2006.01)
*A61K 38/00* (2006.01)
*A61K 31/70* (2006.01)
*A61K 31/715* (2006.01)
*A01N 37/18* (2006.01)
*A01N 43/04* (2006.01)

(52) U.S. Cl. ................... 424/278.1; 424/283.1; 514/23; 514/53

(58) Field of Classification Search ........................ None
See application file for complete search history.

(56) References Cited

U.S. PATENT DOCUMENTS

| | | | |
|---|---|---|---|
| 5,656,272 | A | 8/1997 | Le et al. |
| 5,698,195 | A | 12/1997 | Le et al. |
| 5,741,488 | A | 4/1998 | Feldman et al. |
| 5,919,452 | A | 7/1999 | Le et al. |
| 6,277,969 | B1 | 8/2001 | Le et al. |
| 6,284,471 | B1 | 9/2001 | Le et al. |
| 6,790,444 | B2 | 9/2004 | Le et al. |
| 6,835,823 | B2 | 12/2004 | Le et al. |
| 6,991,791 | B2 | 1/2006 | Le et al. |
| 2001/0027249 | A1 | 10/2001 | Le et al. |
| 2002/0022720 | A1 | 2/2002 | Le et al. |
| 2002/0114805 | A1 | 8/2002 | Le et al. |
| 2002/0141996 | A1 | 10/2002 | Le et al. |
| 2002/0146419 | A1 | 10/2002 | Le et al. |
| 2003/0017584 | A1 | 1/2003 | Le et al. |
| 2003/0054004 | A1 | 3/2003 | Le et al. |
| 2003/0064040 | A1 | 4/2003 | Lukacsko |
| 2003/0133935 | A1 | 7/2003 | Le et al. |
| 2003/0144484 | A1 | 7/2003 | Le et al. |
| 2003/0147891 | A1 | 8/2003 | Le et al. |
| 2003/0175275 | A1 | 9/2003 | Le et al. |
| 2003/0175837 | A1 | 9/2003 | Le et al. |
| 2003/0176676 | A1 | 9/2003 | Le et al. |
| 2003/0180299 | A1 | 9/2003 | Le et al. |
| 2003/0181695 | A1 | 9/2003 | Le et al. |
| 2003/0187231 | A1 | 10/2003 | Le et al. |
| 2003/0194402 | A1 | 10/2003 | Le et al. |
| 2003/0198634 | A1 | 10/2003 | Le et al. |
| 2003/0198641 | A1 | 10/2003 | Le et al. |
| 2003/0204066 | A1 | 10/2003 | Le et al. |
| 2004/0115200 | A1 | 6/2004 | Le et al. |
| 2004/0138427 | A1 | 7/2004 | Le et al. |
| 2005/0037008 | A1 | 2/2005 | Le et al. |
| 2005/0074454 | A1 | 4/2005 | Le et al. |
| 2006/0013816 | A1 | 1/2006 | Le et al. |
| 2006/0018905 | A1 | 1/2006 | Le et al. |
| 2006/0018906 | A1 | 1/2006 | Le et al. |
| 2006/0024310 | A1 | 2/2006 | Le et al. |
| 2006/0211631 | A1 | 9/2006 | Mitsumoto et al. |

FOREIGN PATENT DOCUMENTS

| | | |
|---|---|---|
| EP | 0 689 835 | 1/1996 |
| JP | 8-73351 | 3/1996 |
| JP | 8-505365 | 6/1996 |
| JP | 11-503752 | 3/1999 |
| WO | 92/16553 | 10/1992 |
| WO | 94/08619 | 4/1994 |

OTHER PUBLICATIONS

Hanauer SB, et al. The Lancet 359 (9317):1541-1549, May 4, 2002.*
Hitoshi Asakura, et al., "Efficacy of treatment with chimeric monoclonal antibody (Infliximab) to tumor necrosis factor-α for Crohn's disease in Japan: Evaluation by rapid turnover proteins, and radiologic and endoscopic findings", Journal of Gastroenterology and Hepatology, 16, 2001, pp. 763-769.

(Continued)

*Primary Examiner*—Robert Landsman
(74) *Attorney, Agent, or Firm*—Oblon, Spivak, McClelland, Maier & Neustadt, L.L.P.

(57) ABSTRACT

The present invention provides an antihuman TNF-α antibody activity lowering inhibitor comprising a protein source(s) and/or carbohydrate source(s), in the treatment of inflammatory bowel syndrome with repeated administration of anti-TNF-α antibody; and a kit preparation wherein a freeze-dried antihuman TNF-α antibody and the activity lowering inhibitor in the above repeated administration of the anti-TNF-α antibody are separately contained in a plastic container so that they can communicate with each other. According to the present invention, in the drug therapy to the patients with inflammatory bowel syndrome, therapeutic agents which inhibit the inflammation for long periods without accompanying serious side effects can be provided.

15 Claims, No Drawings

OTHER PUBLICATIONS

M. Takazoe, et al., "Targeted therapy for Crohn's disease (CD)-monoclonal antibody anti-TNF-α therapy", Journal of Japan Society of Coloproctology, 56, 2003, pp. 841-848 and partial English translation.

Torao Tanaka, M.D., et al., "New therapeutic strategy for inflammatory bowel diseases to improve QOL Effect of infliximab treatment for active refractory Crohn's disease", Gastroenterology, 37(5), 2003, pp. 456-463 and partial English translation.

Present, et al., "Infliximab for the Treatment of Fistulas in Patients with Crohn's Disease," The New England Journal of Medicine, vol. 340, No. 18, May 6, 1999, pp. 1398-1405.

Nomura M, et al., Nippon Shokkibyo Gakkai Zasshi, 92(1), Abstract, Jan 1995.

Sanders TA, American J. Clinical Nutrition, 71(Suppl 1), Abstract, Jan 2000.

* cited by examiner

METHODS OF INHIBITING THE LOWERING OF ANTIHUMAN TNF-α ANTIBODY

CROSS-REFERENCE TO RELATED APPLICATIONS

The present application is a divisional of U.S. Ser. No. 11/514,225, tiled on Sep. 1, 2006, which is a continuation of PCT/JP05/03378, filed on Mar. 1, 2005, which claims priority to JP 2004-056343, filed on Mar. 1, 2004.

TECHNICAL FIELD OF THE INVENTION

The present invention relates to therapeutic agents of inflammatory bowel syndrome. More specifically, it relates to anti-TNF-α antibody activity lowering inhibitors or immune deterioration inhibitors in the treatment of inflammatory bowel syndrome with repeated administration of antihuman TNF-α antibody, and kit preparations wherein antihuman TNF-α antibody and protein source thereof and/or carbohydrate source thereof are contained therein.

BACKGROUND OF THE INVENTION

Inflammatory bowel disease (IBD) is etiologically classified into either the specific diseases or nonspecific diseases. Examples of the specific diseases include ischemic colitis and the inflammatory bowel syndrome caused by infection, drugs, chemicals or radiation. In contrast, the nonspecific diseases are also called as idiopathic inflammatory bowel syndrome and broadly classified into colitis (especially, ulcerative colitis (UC)) and Crohn's disease (CD)).

Ulcerative colitis mainly develops in adults aged 30 or under, but it sometimes develops in children or adults aged 50 or older. It forms erosions and ulcers in a mucosal layer or submucosal layer of the large intestinal mucosa, and the clinical symptoms thereof include distinguishing findings such as diarrhea, blood feces, stomachache and weight loss. Though ulcerative colitis was a traditionally relatively rare disease in our country, the number of the patients is increasing rapidly year by year in accordance with recent westernized diet. As the trigger thereof, various causes are thinkable such as enteric bacterial infection theory, dietary allergy theory, vascular disorder theory, autonomic disorder theory and immune abnormality theory, but the details are still unspecified and the fundamental method of the treatment has not yet been established at present.

Crohn's disease mainly develops in young adults, and it is composed of granulomatous inflammatory lesions accompanying fibrillation and ulcers. It is a chronic inflammatory disease which can develop in any area of digestive tubes. Crohn's disease is classified by its lesion area into gastroduodenal type, small bowel type, small and large bowel type, large bowel type, rectum type or subtype. Further, the disease is also classified by its activity determined from CDAI (crohn's disease activity index) classification (by National Cooperative Crohn's Disease Study Group) into the inactive stage, active stage, or extremely seriously ill. The clinical symptoms thereof include the symptoms such as stomachache, diarrhea, fever, anus abnormality like hemorrhoid, and weight loss. Histologically, the strong infiltration of lymphocytes and noncaseating epithelioid granuloma are observed. The detailed causes of Crohn's disease as well as those of ulcerative colitis have not been specified yet.

As for the drug therapy of inflammatory bowel syndrome, for example, steroid hormone, budesonide that is a synthetic steroid and the like are administered to patients with Crohn's disease in the hope of the effect of remission induction. However, there was a problem that side effects occur, such as bone loss, impaired glucose tolerance, hypertension, infections, glaucoma, cataract and gastric ulcer, due to the administration of steroids. In addition to it, salazosulfapyridine (SALAZOPYRINE; 6-oxo-3-((4-(pyridin-2-ylsulfamoyl)phenyl)hydrazinylidene]cyclohexa-1,4-diene-1-carboxylic acid) is administered in the hope of the effect against lesions of the large bowel, but it is reported that there are side effects such as nausea, headache, fever, eruption, hemolytic anemia, epidermal peeling, granulocytopenia, fibrous alveolitis, pancreatitis and male sterility.

In recent years, it has been clarified that inflammation occurs from the interaction between various substances and cells in vivo. It is thought that monocytes and lymphocytes aggregating to an inflammatory site relate to mucosal damages, and inflammatory mediators produced from these cells, especially cytokines are drawn attention to. Among them, TNF-α (Tumor Necrosis Factor-α) is one of the cytokines released from leucocytes and the substance that plays an important role on the defensive function in vivo, but it is also known as the substance that induces and exacerbates the inflammation when released excessively. Since the production of TNF-α increases in the patients with inflammatory bowel syndrome, drugs for inhibiting or neutralizing the production thereof, especially (genetically-modified) Infliximab (Patent Literature 1) of antihuman TNF-α antibody is used to the patients with Crohn's disease in the active stage and with the fistulae (external fistulae) as the drug having the effects such as the improvement of Crohn's disease symptoms and closure of the external fistula (trade name: REMICADE® (trademark) for intravenous drip infusion 100, Tanabe Seiyaku Co., Ltd.; a chimeric mouse/human monoclonal antibody, general name: Infliximab) (Non-patent Literature 2).

Meanwhile, as the antihuman TNF-α antibody decreases immune activity, the careful administration thereof is needed, keeping in mind of infections such as tuberculosis, sepsis, pneumonia and opportunistic infection; or allergic reactions and delayed hypersensitivity. Though the effect of decreasing Crohn's disease activity index (CDAI) is seen in the initial administration, since Crohn's disease requires the long-term continuing treatment and the repeated administration of anti-TNF-α antibody is needed in many cases, such effect is gradually lost, and it causes the problems such as increase in dosage and necessity to switch to the other drug therapies. Further, it has also been reported that the effect of Infliximab is not improved even if the administered dosage thereof is changed to 5, 10, 20 mg per 1 kg of body weight, for example. Therefore, it is necessary to examine the method for having the prolonged effect by small administration dosage. It is also necessary to introduce regression to acute inflammatory diseases in a short period and prolong the effect with inhibiting the expression of the side effects for long periods.

As mentioned above, in the conventional drug therapies including said steroid hormone to the patients with inflammatory bowel syndrome, it has been necessary to administer the drug carefully about the administration time, dosage, period and the like, corresponding to the conditions of the expression of the side effects. Besides, it is difficult to inhibit the inflammation of inflammatory bowel syndrome for long periods without serious side effects, and there were many clinical cases that the inflammation repeats or recurs.

[Patent Literature 1] WO92/16553

[Non-patent Literature 2] Present, D. H. et al., N Engl J Med., 340(18): 1398-1405, 1999

DISCLOSURE OF THE INVENTION

The object of the present invention is to provide therapeutic agents that inhibit the inflammation for long periods without accompanying serious side effects in the drug therapy to patients with inflammatory bowel syndrome.

The inventors have studied the above therapeutic problems in the administration of the antihuman TNF-α antibody to be solved and they have completed the present invention.

Namely, the present invention relates to:

[1] an antihuman TNF-α antibody activity lowering inhibitor comprising a protein source(s) and/or carbohydrate source(s), in the treatment of inflammatory bowel syndrome with repeated administration of anti-TNF-α antibody;

[2] the antihuman TNF-α antibody activity lowering inhibitor according to [1], wherein the inflammatory bowel syndrome is Crohn's disease;

[3] the antihuman TNF-α antibody activity lowering inhibitor according to [1], wherein Crohn's disease is in the active stage and/or it accompanies the external fistula;

[4] the antihuman TNF-α antibody activity lowering inhibitor according to [1], which further has an immune deterioration inhibiting effect and/or infection preventing effect;

[5] the antihuman TNF-α antibody activity lowering inhibitor according to [1], which is orally or enterally administered;

[6] the antihuman TNF-α antibody activity lowering inhibitor according to [1], which is administered in the central vein;

[7] a kit preparation wherein a freeze-dried antihuman TNF-α antibody and the antihuman TNF-α antibody activity lowering inhibitor in the repeated administration of the above anti-TNF-α antibody are separately contained in a plastic container so that they can communicate with each other; and

[8] an immune deterioration inhibitor and/or infection preventing agent in the repeated administration of anti-TNF-α antibody, which comprises a protein source(s) and/or carbohydrate source(s) in the treatment of inflammatory bowel syndrome with antihuman TNF-α antibody.

BEST MODE FOR CARRYING OUT THE INVENTION

The protein source(s) which is an active ingredient(s) of anti-TNF-α antibody activity lowering inhibitors of the present invention may be any proteins that are useful for supplying nutrients, and it may be either animal proteins or vegetable proteins. As for animal proteins, milk proteins are preferable, and lactose-reduced milk protein and casein are particularly preferable. As for vegetable proteins, soybean protein isolates are preferable. Two or more kinds of proteins may be dispensed. In addition, the protein source(s) may be peptide of a hydrolyzed protein(s). When considering protein allergy, the protein source(s) is more preferably an amino acid(s). As for amino acid(s), they are not particularly limited only if they are the amino acids usually used for supplying nutrients, such as infusions and enteral feeding products, but they are preferably crystalline amino acids.

Amino acids may be either D-form, L-form or DL-form, but L-amino acids axe preferable. More specifically, they include L-isoleucine, L-leucine, L-valine, L-lysine, L-methionine, L-phenylalanine, L-threonine, L-triptophan, L-alanine, L-arginine, L-asparaginic acid, L-cystein, L-glutaminic acid, L-histidine, L-proline, L-serine, L-tyrosine and glycin. These amino acids can be used by itself or used (dispensed) by combining several kinds thereof. The combination of several kinds thereof is preferable, and it is more preferably the combined use of eight (8) kinds of essential amino acids, that is, L-triptophan, L-methionine, L-lysine, L-phenylalanine, L-leucine, L-isoleucine, L-valine and L-threonine. It is further more preferably the combined use of eight kinds of essential amino acids and nonessential amino acids. Besides, it is particularly preferable from the aspect of preservation stability to dispense branched-chain amino acids of L-valine, L-isoleucine and L-leucine.

When the protein source(s) is an amino acid(s), it is preferable to contain the amino acids at least in the following contents by dry weight.

| | |
|---|---|
| L-isoleucine | 2.0 to 8.0 W/W % |
| L-leucine | 4.0 to 15.0 W/W % |
| L-lysine | 4.0 to 15.0 W/W % |
| L-methionine | 2.0 to 6.0 W/W % |
| L-phenylalanine | 4.0 to 12.0 W/W % |
| L-threonine | 1.0 to 8.0 W/W % |
| L-triptophan | 0.5 to 3.0 W/W % |
| L-valine | 2.0 to 6.0 W/W % |
| L-histidine | 1.0 to 8.0 W/W % |
| L-arginine | 5.0 to 9.0 W/W % |
| L-alanine | 4.0 to 8.0 W/W % |
| L-asparaginic acid | 2.0 to 15.0 W/W % |
| L-glutamine | 0 to 15.0 W/W % |
| Glycin | 1.0 to 12.0 W/W % |
| L-proline | 2.0 to 6.0 W/W % |
| L-serine | 1.0 to 10.0 W/W % |
| L-tyrosine | 0.1 to 3.0 W/W % |
| L-cystein | 0 to 10.0 W/W % |
| L-glutaminic acid | 0 to 10.0 W/W % |

Each amino acid does not always have to be used as a free amino acid, and it may be used in the forms of salts of inorganic acids or organic acids; and ester forms that can be hydrolyzed in vivo. Further, it may be used in the form of dipeptides wherein the same kind or different kinds of amino acids form a peptide bond. As the protein source(s), it is preferable to contain at least one kind of milk proteins, vegetable proteins, and amino acids. Particularly, in the repeated administration of the antihuman TNF-α antibody, the activity lowering inhibiting effect can successfully work by containing amino acids as the protein source(s). Therefore, it is preferable to contain only amino acids as the protein source(s).

The carbohydrate source(s) which is an active ingredient(s) of anti-TNF-α antibody activity lowering inhibitors of the present invention is preferably sugars, and they include monosaccharide, disaccharide, and polysaccharide. More specifically, they include glucose, fructose, mannose, galactose, sucrose, sugar (it may be purified sucrose), maltose, lactose, dextrin, maltodextrin, starch, corn starch, soybean oligosaccharide, and sugar alcohols. Two or more kinds of these sugars may be dispensed. In the repeated administration of the antihuman TNF-α antibody, the activity lowering inhibiting effect can successfully work by containing at least one kind of sugar(s) selected from the group consisting of glucose, fructose, maltose, sorbitol, xylitol and glycerin as the carbohydrate source(s).

In the anti-TNF-α antibody activity lowering inhibitors of the present invention, the protein source(s) and carbohydrate source(s) can be contained by itself, but they may be combined and contained therein.

The anti-TNF-α antibody activity lowering inhibitors of the present invention can also contain a lipid source(s) in addition to the protein source(s) and/or carbohydrate source(s). The lipid source(s) is preferable since it can suitably activate the activity lowering inhibiting effect. The lipid source(s) is not particularly limited, and vegetable oils and animal oils are preferable. Vegetable oils include soybean oil, perilla oil and corn oil, and soybean oil is preferable. Further, as fats and oils containing a high proportion of ω3 fatty acids, perilla oil may be contained. As for animal oils, fish oils containing ω3 fatty acids such as eicosapentaenoic acid and docosahexaenoic acid are preferable. Two or more kinds of the above lipids may be dispensed, and it is more preferable to contain fats containing at least one kind of ω3 fatty acid(s), which is selected from the group consisting of α-linolenic acid, eicosapentaenoic acid and docosahexaenoic acid. The preferable content of each component is, by dry weight, 5 to 30 W/W % (more preferably 8 to 20 W/W %) of the protein source(s); 40 to 90 W/W % (more preferably 70 to 85 W/W %) of the carbohydrate source(s); and 0 to 30 W/W % (more preferably 0.01 to 25 W/W %, and further more preferably 0.1 to 1 W/W %) of the lipid source(s).

As the first preferable embodiment of the antihuman TNF-α antibody activity lowering inhibitors of the present invention, there are nutrient compositions for the oral or enteral administration.

The content of each component of the above compositions can be any if only it is within the above range. Particularly, in case of the liquid compositions, it is preferable that the protein source(s) is within 1 to 10 W/V %; the carbohydrate source(s) is within 5 to 30 W/V %; and the lipid source(s) is within 0.5 to 20 W/V %. The nutrient compositions having such contents of the components may be in the forms of enteral feeding products or liquid diets.

In addition, in case that the protein source(s) is all amino acids, the amount of each amino acid in the composition is preferably the following contents by dry weight.

| | | |
|---|---|---|
| L-isoleucine | 0.2 to 1.5 | W/W % |
| L-leucine | 0.5 to 2.0 | W/W % |
| L-lysine | 0.5 to 2.0 | W/W % |
| L-methionine | 0.2 to 1.5 | W/W % |
| L-phenylalanine | 0.5 to 2.0 | W/W % |
| L-threonine | 0.2 to 1.5 | W/W % |
| L-tryptophan | 0.05 to 0.5 | W/W % |
| L-valine | 0.2 to 1.5 | W/W % |
| L-histidine | 0.5 to 2.0 | W/W % |
| L-arginine | 0.5 to 2.5 | W/W % |
| L-alanine | 0.5 to 2.0 | W/W % |
| L-asparaginic acid | 1.0 to 4.0 | W/W % |
| L-glutamine | 1.0 to 4.0 | W/W % |
| Glycin | 0.2 to 1.5 | W/W % |
| L-proline | 0.2 to 1.5 | W/W % |
| L-serine | 0.5 to 2.5 | W/W % |
| L-tyrosine | 0.05 to 0.5 | W/W % |

In this case, it is preferable that the carbohydrate is dextrin and the lipid is soybean oil.

More specifically, there is ELENTAL® (trademark) which has the composition shown in Tables 1 and 2 and is marketed as an enteral feeding product.

TABLE 1

| Components | Content (g) in 133 g |
|---|---|
| Amino acid | |
| L-isoleucine | 1.068 |
| L-leucine | 1.495 |
| Lysine hydrochloride | 1.476 |
| L-methionine | 1.077 |

TABLE 1-continued

| | |
|---|---|
| L-phenylalanine | 1.448 |
| L-threonine | 0.87 |
| L-tryptophan | 0.251 |
| L-valine | 1.165 |
| L-histidine hydrochloride (monohydrate) | 0.833 |
| L-arginine hydrochloride | 1.87 |
| L-alanine | 1.495 |
| L-asparaginic acid magnesium/potassium | 1.722 |
| L-asparaginic acid sodium (monohydrate) | 1.442 |
| L-glutamine | 3.212 |
| Glycin | 0.839 |
| L-proline | 1.048 |
| L-serine | 1.927 |
| L-tyrosine | 0.184 |
| (Total) | 23.422 |
| Carbohydrate | |
| Dextrin | 105.42 |
| Lipid | |
| Soybean oil | 0.846 |
| Minerals | |
| Sodium citrate (dihydrate) | 1.024 |
| Potassium chloride | 0.25 |
| Calcium glycerophosphate | 1.371 |
| Ferric gluconate (dihydrate) | 0.0258 |
| Zinc sulfate (heptahydrate) | 0.0131 |
| Manganese sulfate (pentahydrate) | 0.00217 |
| Copper sulfate (pentahydrate) | 0.00137 |
| Potassium iodide | 0.0000326 |
| Vitamins | |
| Thiamine hydrochloride | 0.000322 |
| Riboflavin sodium phosphate | 0.000426 |
| Pyridoxine hydrochloride | 0.000444 |
| Cyanocobalamin | 0.0000012 |
| Calcium pantothenate | 0.00198 |
| Nicotinic-acid amide | 0.00366 |
| Folic acid | 0.000073 |
| Biotin | 0.000065 |
| Choline bitartrate | 0.02981 |
| Ascorbic acid | 0.01297 |
| Retinol acetate granules | 0.0215 |
| Tocopherol acetate granules | 0.02744 |
| Ergocalciferol | 0.0000021 |
| Phytonadione | 0.000015 |

Additives (potassium sorbate, polysorbate 80, aspartame (L-phenylalanine compound), flavoring agent)

TABLE 2

| Components | Content (g) in 80 g |
|---|---|
| Amino acid | |
| L-isoleucine | 0.642 |
| L-leucine | 0.899 |
| L-lysine hydrochloride | 0.888 |
| L-methionine | 0.648 |
| L-phenylalanine | 0.871 |
| L-threonine | 0.523 |
| L-tryptophan | 0.151 |
| L-valine | 0.701 |
| L-histidine hydrochloride | 0.501 |
| L-arginine hydrochloride | 1.125 |
| L-alanine | 0.899 |
| L-asparaginic acid magnesium/potassium | 1.036 |
| L-asparaginic acid sodium monohydrate | 0.867 |
| L-glutamine | 1.932 |
| Glycin | 0.505 |
| L-proline | 0.630 |

TABLE 2-continued

| Components | Content (g) in 80 g |
|---|---|
| L-serine | 1.159 |
| L-tyrosine | 0.110 |
| (Total) | 14.087 |
| Carbohydrate | |
| Dextrin | 63.41 |
| Lipid | |
| Soybean oil | 0.509 |
| Minerals | |
| Sodium citrate | 0.616 |
| Potassium chloride | 0.150 |
| Calcium glycerophosphate | 0.825 |
| Ferrous gluconate dihydrate | 0.0155 |
| Zinc sulfate | 0.00788 |
| Manganese sulfate pentahydrate | 0.00130 |
| Copper sulfate | 0.00082 |
| Potassium iodide | 0.0000196 |
| Vitamins | |
| Thiamine hydrochloride | 0.000194 |
| Riboflavin sodium phosphate | 0.000256 |
| Pyridoxine hydrochloride | 0.000267 |
| Cyanocobalamin | 0.0000007 |
| Calcium pantothenate | 0.00119 |
| Nicotinic-acid amide | 0.00220 |
| Folic acid | 0.000044 |
| Biotin | 0.000039 |
| Choline bitartrate | 0.01793 |
| Ascorbic acid | 0.00780 |
| Retinol acetate | (648 IU) |
| Tocopherol acetate | 0.00330 |
| Ergocalciferol | 0.0000013 |
| Phytonadione | 0.000009 |

Additives (potassium sorbate, polysorbate 80, aspartame (L-phenylalanine compound), flavoring agent, propylene glycol, soybean lecithin citric acid, lactose, carmellose sodium)

In addition, the compositions for the oral or enteral administration of the present invention may be in suitable dosage forms. For example, they are prepared as powders, subtle granules, granules, tablets, capsules, and solutions. Since the liquid form is preferable in the administration, it is preferable that the compositions are the solutions or the dosage forms that can be dissolved in some water and the like in use. Among the above dosage forms, the compositions are preferably prepared to flavored preparations so that elderly people and children can take them easily. In preparing the liquid form, it is preferable to be diluted by water so that the composition becomes about 1 kcal per 1 cc.

Additives for adding to powders, subtle granules, granules, tablets, capsules and the like include excipients, e.g. lactose, glucose, D-mannitol, starch, crystalline cellulose, calcium carbonate, kaolin, light anhydrous silicic acid and trehalose; binders, e.g. starch glue solution, gelatin solution, hydroxypropyl cellulose, hydroxypropyl methylcellulose, polyvinyl pyrrolidone and ethanol; disintegrating agents, e.g. starch, gelatin powder, carboxymethyl cellulose and carboxymethyl cellulose calcium salt; lubricants, e.g. magnesium stearate and talc; and coating agents, e.g. hydroxypropyl cellulose, hydroxypropyl methylcellulose, acetyl cellulose, sucrose and titanium oxide. The other coloring and flavoring agents are added thereto, if necessary. As for the additives for adding to internal drug solutions, there are, for example, preservatives, e.g. benzoic acid, p-hydroxybenzoate ester and sodium dehydxoacetate; suspending agents or emulsifiers, e.g. gum arabic, tragacanth, carboxymethyl cellulose sodium salt, methylcellulose, yolk and surfactants; and sweetening/acidulating agents, e.g. trehalose and citric acid. The other coloring and stabilizing agents axe added thereto, if necessary, and solutions used therefor are mainly purified water, but ethanol, glycerin, propylene glycol, and the like are also usable.

These preparations can be prepared in accordance with the ordinary methods, by using each active ingredient by itself, by mixing/granulating them with a pharmaceutically and pharmacologically acceptable additive(s) corresponding to each dosage form; or dissolving them in a suitable solvent(s) and then emulsifying or suspending them, and further mixing the reaction solution with a suitable base(s).

The administered dosage is preferably 80 to 640 g (300 to 2400 kcal) per a day in adults, and more preferably approximately 1200 kcal, though it can be adjusted accordingly depending on the age, body weight, symptom and the like of patients.

As for the administration methods, for example, they are injected into the duodenum or empty jejunum through nasal tube, gastric fistula or enteric fistula, or orally administered.

The administration period is not particularly limited during the patients are affected by inflammatory diseases, and it is preferable to be administered at least during the treatment period with the antihuman TNF-α antibody. In addition, it may be administered before starting the treatment with the antihuman TNF-α antibody or continued to be administered after the completion of the treatment with the antihuman TNF-α antibody. It is further more preferable that it is continuously administered every day beginning from the start of the repeated administration of the antihuman TNF-α antibody during the administration period of the antihuman TNF-α antibody.

When the activity lowering inhibitors of the present invention are prepared to solutions in the repeated administration of the antihuman TNF-α antibody, the solution viscosity is preferably 5 mPa·S or lower, and the solution having this viscosity range can be enterally administered easily through nasal tube, gastric fistula or enteric fistula. On the other hand, in case of bedridden patients, when the solutions having a low viscosity are administered to them, there are problems such as vomiting by reflux thereof in the esophagus and a trigger of reflux pneumonia. For those patients, it is preferable to add a thickener(s) for adding the solution viscosity to the compositions of the present invention. As the thickeners, it is preferable to use alginic acid sodium, alginic acid or carrageenans. It is also preferable that the thickener(s) is added so that the solution viscosity can be prepared to 300 mPa·S or higher.

It is also possible to add dietary fibers such as water-soluble dietary fibers and insoluble dietary fibers to antihuman TNF-α antibody activity lowering inhibitors of the present invention. The added amount of dietary fibers is preferably 1 to 30 g per a day, more preferably 5 to 15 g and particularly preferably 3 to 8 g. As the dietary fibers, the water-soluble dietary fibers include pectin, methoxy pectin, galactomannan, alginic acid and salt thereof, agar extracted from seaweed containing galactan such as Gelidium and false Ceylon moss, carboxymethyl cellulose and salt thereof. The insoluble fibers include fibers obtained from plants such as apple fiber, corn fiber and pineapple fiber; dried vegetables such as those of broccoli, cauliflower, cabbage and spinach; and soybeans and flour bran composed of cellulose, hemicellulose, carrageenan, lignin and the like.

The second preferable embodiment of antihuman TNF-α antibody activity lowering inhibitors of the present invention is to be prepared as preparations for being administered in the central vein. The contents of each active ingredient can be arbitrarily prepared as infusion components as referred to the preparations for oral or enteral administration. The same applies to the administered dosage.

More specifically, there is PNTWIN® (trademark) which has the composition shown in following Table 3 and is marketed as a high-caloric infusion.

TABLE 3

| Component | Content (g/2 L) |
|---|---|
| Amino acids | |
| L-isoleucine | 2.240 |
| L-leucine | 5.000 |
| L-lysine acetate | 4.960 |
| L-methionine | 1.400 |
| L-phenylalanine | 3.740 |
| L-threonine | 2.600 |
| L-triptophan | 0.520 |
| L-valine | 1.800 |
| L-alanine | 2.480 |
| L-arginine | 3.160 |
| L-asparaginic acid | 1.520 |
| L-cystein | 0.400 |
| L-glutamic acid | 2.600 |
| L-histidine | 2.400 |
| L-proline | 1.320 |
| L-serine | 0.880 |
| L-tyrosine | 0.140 |
| Glycin | 4.280 |
| (Total) | 41.440 |
| Carbohydrate | |
| Glucose | 240.0 |
| Minerals | |
| Sodium chloride | 5.840 |
| Potassium carbonate | 4.320 |
| Potassium dihydrogen phosphate | 2.176 |
| Magnesium sulfate | 1.480 |
| Calcium gluconate | 3.584 |
| Zinc sulfate | 0.011504 |
| Additives | |
| Sodium bisulfite | 0.060 |
| Citric acid | adequate dose |

Further, for convenience in use, the antihuman TNF-α antibody activity lowering inhibitors of the present invention may be packed with the antihuman TNF-α antibody together and produced as a kit product. In addition, when the antihuman TNF-α antibody is prepared as a freeze-dried product, for convenience of administration and in order to have usefulness of sterile preparation, it may be in the form of a kit preparations wherein the freeze-dried antihuman TNF-α antibody and the infusion are separately housed in a plastic container so that they can communicate with each other.

According to the present invention, the preferred inhibiting effect against activity lowering in the repeated administration of antihuman TNF-α antibody can be expected to patients with Crohn's disease among those with inflammatory bowel syndrome. Further, the more preferable effect can be obtained to the patients with Crohn' disease in the active stage and/or with the external fistula.

The antihuman TNF-α antibody activity lowering inhibitors of the present invention concurrently have the immune deterioration inhibiting effect and have the effect for inhibiting side effects accompanied by administration of the antibody.

As the antihuman TNF-α antibody of the present invention, the antibody which has high affinity for the TNF-α of human in vivo and concurrently has the neutralizing effect of the activity can be used.

The affinity for the human TNF-α preferably has at least Ka $10^8 M^{-1}$ and more preferably at least Ka $10^9 M^{-1}$. In addition, it is preferable to have a strong in vivo human TNF-α stopping power and/or neutralizing capacity (such as the capacity to neutralize the cytopathy activity of the human TNF-α, the capacity to block the TNF-induced secretion of IL-6 and the capacity to block the TNF-induced procoagulant activity. It is also preferable to have a high specificity for the human TNF-α.

As the antihuman TNF-α antibody used in the present invention, a monoclonal antibody or a part thereof can be used. Such antibodies include a chimeric antibody, humanized antibody, human antibody, primatized antibody, surface processing antibody, single-stranded antibody, and TNF-receptor-IgG-Fc fusion protein. It is desirable that these antibodies are low in immunogenicity and toxicity in vivo.

The chimeric antibody is an immunoglobulin molecule wherein two or more parts derived from different animal species are bonded. Generally, the variable region of the chimeric antibody is derived from the antibody of mammals but human such as a mouse monoclonal antibody and is combined with the immunoglobulin constant region thereof. The chimeric antibody includes a monovalent, divalent or polyimmunoglobulin. The chimeric antibody and the production methods thereof are described in EP 1714961, EP 173494, WO86/01533, EP184187, WO87/02671, WO910996 and WO92/11383. Further, Infliximab is a preferable drug Infliximab (general name: Infliximab, trade name: REMICADE) is a chimeric monoclonal antibody which consists of the antigen-binding variable region of the mouse antihuman TNF-α mouse IgG1 antibody and the constant region of the human IgG1 kappa immunoglobulin. Infliximab can be produced in accordance with the production method described in WO92/16553.

As for the humanization of the antibody and surface processing thereof, they are described in U.S. Pat. No. 5,225,539, EP239400, EP519596 and EP592106.

The human antibody and the production methods thereof are described in WO92/03918, WO91/10741, WO96/33735, WO96/34096, and WO97/29131. Further, there is Adalimumab, for example.

As for TNF receptors in TNF-receptor-IgG-Fc fusion protein, TNFRII(p75) is preferable and its example is Etanercept.

The anti-TNF-α antibody of the present invention is more preferably Infliximab, but of course the effects of the present invention can be obtained even when using Adalimumab or Etanercept, that are used in the treatment of rheumatism as well as Infliximab, to the patients with inflammatory bowel syndrome.

Due to the anti-TNF-α antibody activity lowering inhibitors of the present invention, lowering of antihuman TNF-α antibody activity can be effectively inhibited when, in the treatment of inflammatory bowel syndrome, repeatedly administering antihuman TNF-α antibody that is an excellent drug in the drug therapy to the patients with inflammatory bowel syndrome.

Further, due to the immune deterioration inhibitors and/or infection preventing agents of the present invention in the repeated administration of anti-TNF-α antibody, the immune deterioration can be inhibited and/or the infections can be prevented when, in the treatment of inflammatory bowel syndrome, repeatedly administering antihuman TNF-α antibody that is an excellent drug in the drug therapy to the patients with inflammatory bowel syndrome.

The high medical cost is required for repeatedly administering the anti-TNF-α antibody, and according to the present invention, the number of doses can be decreased by extending the administration intervals in the repeated administration and, therefore, the medical cost can be reduced.

Next, Examples will further illustrate the present invention in detail. The following Examples only explain the present invention and do not particularly limit the invention.

EXAMPLES

Example 1

A patient is a 31-year-old male, and he is the patient with small intestine/large intestine type Crohn's disease that began from age 25. By August 2002, Crohn's disease repeatedly recurred and he was hospitalized three times.

In July 2002, since Crohn's disease recurred again accompanied by stomachache, diarrhea and fever, 5 mg/kg of Infliximab (REMICADE® (trademark) 100 for drip infusion) under the enteral administration of 1200 kcal of ELENTAL® (trademark) was administered to the patient. The clinical activity index of Crohn's disease before the administration was 186 (150 or higher fall into the active stage). However, the index was lowered to 67 two weeks after the administration. During the period, an open longitudinal ulcer(s) seen in the transverse colon and sigmoid colon was cicatrized. After that, thought the patient was treated with the home enteral nutritional therapy, the symptoms recurred in February 2003 and CDAI increased up to 230. Continuing the enteral administration of ELENTAL® (trademark), Infliximab (5 mg/kg) was administered for the second time. Then, CDAI was lowered again to 63 two weeks later. Further, two months after that, CDAI similarly increased up to 250 under the administration of ELENTAL® (trademark). Therefore, Infliximab (5 mg/kg) was administered for the third time, and CDAI was lowered to 80 two weeks later. Before and after the administration for the third time, it was confirmed that an open ulcer(s) of the sigmoid colon was cicatrized. Similarly, though CDAI increased in the 50th week, 68th week and 83rd week from the first administration, CDAI of 147 to 275 decreased to 50 to 80 84 weeks later by the fourth, fifth and sixth time administrations of Infliximab. During that time, administration of ELENTAL was continued.

Usually, the repeated administration of Infliximab promotes production of antibody and, therefore, its effect weakens in the repeated administration. However, in the above case, it is assumed that the effect of Infliximab could be preserved due to the combination of ELENTAL.

In the present Example, in the course of the administration of Infliximab from the first to sixth times, the fever was seen when the symptom recurred. However, there was no finding of indication of infection in organs of respiration or in a urinary tract and so it was not necessary to administer antimicrobials. In addition, tuberculosis bacterium infection was not seen, which is one of the serious side effects of Infliximab. Thus, combination of ELENTAL® (trademark) reduce concurrent infections after the administration of Infliximab, and the effect of inhibiting immune deterioration can be expected.

I claim:

1. A method of inhibiting the lowering of antihuman TNF-α antibody activity comprising administering to a subject suffering from inflammatory bowel disease that has or is undergoing a treatment regimen involving repeated administration of anti-TNF-α antibody an effective amount of a protein source(s), carbohydrate source(s) or a combination thereof, wherein the protein source(s) comprises the amino acids at least in the following contents by dry weight of the protein source(s):

| L-isoleucine | 2.0 to 8.0 W/W % |
|---|---|
| L-leucine | 4.0 to 15.0 W/W % |
| L-lysine | 4.0 to 15.0 W/W % |
| L-methionine | 2.0 to 6.0 W/W % |
| L-phenylalanine | 4.0 to 12.0 W/W % |
| L-threonine | 1.0 to 8.0 W/W % |
| L-triptophan | 0.5 to 3.0 W/W % |
| L-valine | 2.0 to 6.0 W/W % |
| L-histidine | 1.0 to 8.0 W/W % |
| L-arginine | 5.0 to 9.0 W/W % |
| L-alanine | 4.0 to 8.0 W/W % |
| L-asparaginic acid | 2.0 to 15.0 W/W % |
| L-glutamine | 0 to 15.0 W/W % |
| Glycin | 1.0 to 12.0 W/W % |
| L-proline | 2.0 to 6.0 W/W % |
| L-serine | 1.0 to 10.0 W/W % |
| L-tyrosine | 0.1 to 3.0 W/W % |
| L-cystein | 0 to 10.0 W/W % |
| L-glutaminic acid | 0 to 10.0 W/W %, | and wherein the carbohydrate source(s) is at least one kind of sugar selected from the group consisting of glucose, fructose, maltose, sorbitol, xylitol and glycerin.

2. The method according to claim 1, wherein the protein source(s) is animal proteins, vegetable proteins or a combination thereof.

3. The method according to claim 1, wherein the protein source(s) is milk proteins, soybean protein isolates or a combination thereof.

4. The method according to claim 1, further comprising administering a lipid source(s).

5. The method according to claim 4, wherein the lipid source(s) comprises fats containing at least one kind of ω3 fatty acid(s), which is selected from the group consisting of α-linolenic acid, eicosapentaenoic acid and docosahexaenoic acid.

6. The method according to claim 4, wherein the protein source(s), carbohydrate source(s), and lipid source(s) are administered in a single composition and said protein source(s) is in an amount of 5 to 30 W/W % by dry weight; the carbohydrate source(s) is in an amount of 40 to 90 W/W % by dry weight; and the lipid source(s) is in an amount of 0 to 30 W/W % by dry weight, wherein the weight percentage is relative to the total weight of same composition.

7. The method according to claim 6, wherein amounts of the protein source(s), the carbohydrate source(s) and the lipid source(s), relative to the total weight of the composition, are the following amounts by dry weight:

| Protein source(s); | |
|---|---|
| L-isoleucine | 0.2 to 1.5 W/W % |
| L-leucine | 0.5 to 2.0 W/W % |
| L-lysine | 0.5 to 2.0 W/W % |
| L-methionine | 0.2 to 1.5 W/W % |
| L-phenylalanine | 0.5 to 2.0 W/W % |
| L-threonine | 0.2 to 1.5 W/W % |
| L-triptophan | 0.05 to 0.5 W/W % |
| L-valine | 0.2 to 1.5 W/W % |
| L-histidine | 0.5 to 2.0 W/W % |
| L-arginine | 0.5 to 2.5 W/W % |
| L-alanine | 0.5 to 2.0 W/W % |
| L-asparaginic acid | 1.0 to 4.0 W/W % |
| L-glutamine | 1.0 to 4.0 W/W % |
| Glycin | 0.2 to 1.5 W/W % |
| L-proline | 0.2 to 1.5 W/W % |

-continued

| | |
|---|---|
| L-serine | 0.5 to 2.5 W/W % |
| L-tyrosine | 0.05 to 0.5 W/W % |
| Carbohydrate source(s); | |
| Dextrin | 70 to 85 W/W % |
| Lipid source(s); | |
| Soybean oil | 0.1 to 10 W/W %. |

8. The method according to claim 1, wherein the antihuman TNF-α antibody is a monoclonal antibody selected from the group consisting of a chimeric antibody, humanized antibody and human antibody.

9. The method according to claim 8, wherein the antihuman TNF-α antibody is at least one selected from the group consisting of Infliximab, Adalimumab and Etanercept.

10. The method according to claim 9, wherein the antihuman TNF-α antibody is Infliximab.

11. The method according to claim 1, wherein the inflammatory bowel disease is Crohn's disease.

12. The method according to claim 11, wherein the Crohn's disease is in the active stage and/or it accompanies the external fistula.

13. The method according to claim 1, wherein said administering further has an immune-deterioration-inhibiting effect, reduces concurrent infections or a combination thereof.

14. The method according to claim 1, wherein said administering is orally or enterally.

15. The method according to claim 1, wherein said administering is in the central vein.

* * * * *